United States Patent [19]

Ogasa et al.

[11] 4,226,847

[45] Oct. 7, 1980

[54] LATEX POLYMER SENSITIZED WITH STEROID-SERUM ALBUMIN CONJUGATE, PREPARATION AND TEST THEREWITH

[75] Inventors: Katsuhiro Ogasa, Yokohama; Morio Kuboyama, Tokyo; Minoru Saito, Komae; Tsutomu Kudo, Kawasaki; Yoshitsugu Harada, Yokohama; Akio Kawashiri, Fujimi; Eiji Takahashi, Tokyo, all of Japan

[73] Assignee: Morinaga Milk Industry Co., Ltd., Tokyo, Japan

[21] Appl. No.: 917,254

[22] Filed: Jun. 20, 1978

[30] Foreign Application Priority Data

Jun. 21, 1977 [JP] Japan .................................. 52/72775

[51] Int. Cl.$^2$ ..................... A61K 39/00; A61K 31/74; G01N 31/00; G01N 33/16
[52] U.S. Cl. ................................. 424/12; 23/230 B; 260/8; 260/112 R; 260/112 B; 260/121; 424/8; 424/78
[58] Field of Search ............................... 424/8, 12, 78; 23/230 B; 260/8, 112 R, 112 B, 121

[56] References Cited

FOREIGN PATENT DOCUMENTS

| | | |
|---|---|---|
| 73-49918 | 7/1973 | Japan . |
| 74-11407 | 3/1974 | Japan . |
| 75-82230 | 7/1975 | Japan . |
| 75-123819 | 9/1975 | Japan . |
| 76-112513 | 10/1976 | Japan . |

OTHER PUBLICATIONS

Atsumi et al., Immunochemistry, vol. 8, 1971 pp. 271–279.
Erlanger et al., J. Biol. Chem., vol. 233, May, 1959, pp. 1090–1094.

Primary Examiner—Anna P. Fagelson
Attorney, Agent, or Firm—Oblon, Fisher, Spivak, McClelland & Maier

[57] ABSTRACT

Latex reagents for quantitative assay of a variety of steroid hormones or metabolites thereof which are contained in body fluid or excreted fluid of human beings comprise latex particles which are immunologically sensitized with a conjugate selected from a variety of steroid-serum albumin conjugates in which the steroid to be detected is bonded to serum albumin in a very small ratio ranging from 0.5 to 7 molecules per 1 molecule of the serum albumin used.

Sensitization of latex particles with such a conjugate is performed using a limited amount dependent on the bonding ratio of steroid molecules per molecule of serum albumin in the conjugate and the particle size of the latex used.

The latex reagents show very high sensitivity amounting to 0.2–0.04 nmole steroid equivalent/ml.

16 Claims, No Drawings

LATEX POLYMER SENSITIZED WITH STEROID-SERUM ALBUMIN CONJUGATE, PREPARATION AND TEST THEREWITH

BACKGROUND OF THE INVENTION

It has been known that the quantity of steroid hormones and/or metabolites thereof contained in human body fluid or excreted fluid is correlated with physiological and pathological states of human beings. Therefore quantitative analysis of steroid hormones and/or metabolites thereof is useful for purposes of diagnosis and clinical examination.

However, the quantity of steroid hormones and metabolites thereof contained in human body fluid or excreted fluid is generally small, and the variation in quantity of steroid hormones and metabolites thereof due to a specific physiological or pathological states is also small.

Consequently quantitative analysis of steroid hormones and/or metabolites thereof requires extremely high accuracy.

Recent developments in analytical instruments make it possible to conduct extremely accurate quantitative analysis. Such instruments are highly elaborate, and installation and maintainance of such instruments involve high costs in general. Furthermore, manipulation of such instruments is not easy for persons who are not skilled, and often requires troublesome and time-consuming preliminary treatment of samples to be analyzed.

Therefore it is significant to provide a means for enabling accurate and rapid quantitative detection of steroid hormones and/or metabolites thereof without necessitating special training and special instruments.

It has been known that quantitative detection of steroids can be accomplished by immunological methods. One of the typical immunological methods utilizes the specificity of the antigen-antibody reaction and visibility of the agglutination and agglutination inhibition reaction thereof. More specifically, in the typical prior art, the type of steroid to be detected is bonded to protein to give a steroid-protein conjugate, then a reagent is prepared having latex particles sensitized with the conjugate and antiserum is prepared by injecting the conjugate into a mammal. The thus obtained antiserum may react with the steroid to be detected and also may react with the reagent. Therefore if a given quantity of a test sample of human body fluid or excreted fluid is collected and mixed with a given quantity of said antiserum, a reaction takes place therebetween. Then a given quantity of the reagent is added to the liquid mixture of the test sample and the antiserum. If an excess amount of antiserum remains in the fluid mixture of said test sample and the antiserum, antigen-antibody reaction between the remaining antiserum and the reagent can be observed as an agglutination reaction, and if the antiserum is just neutralized with the steroid contained in the test sample or an excess amount of steroid remains in the fluid mixture no antigen-antibody reaction occurs, and this can be observed as and agglutination inhibition reaction. Therefore, if serially diluted test samples are tested with the antiserum, which is used at a predetermined titer, and the reagent, quantitative assay of the steroid and/or metabolites thereof can be performed.

One of such prior art methods is disclosed in Japanese Early Opened Patent application Publication No. 51-112513 (Filing Date: Mar. 25, 1975; Inventor: Osamu Kanemitsu; Applicant: Asahi Kasei Kogyo Kabushiki Kaisha; Date of Laying-Open: Oct. 5, 1976). This first prior art publication refers to a method for immunological quantitative assay of dehydroepiandrosterone sulphate (which is an intermediate in the biosynthesis of a sex hormone), but this prior art adds nothing new to the aforementioned typical prior art. Though these methods of the prior art provide useful diagnostic testing methods, it has been strongly desired to increase the sensitivity of such immunological quantitative assay, since this makes it possible to detect slighter variations of steroid quantity and to provide increased accuracy for conventional use.

Meanwhile, human body fluid or excreted fluid usually contains many kinds of compounds besides steroids, and the amounts of these compounds are usually far greater than the steroid content. Some of these compounds, for example, protein and saccharide, affect immunological assay, and it is necessary to remove them or dilute the body fluid or excreted fluid to be tested to the extent where no interference is caused. Removal of the interfering compounds requires a complicated process, and in clinical analysis which requires simplicity and rapidity, it is necessary to dilute the fluid to be tested. This makes it necessary to increase the sensitivity of such immunological assay.

Adjustment of sensitivity is referred to in the Japanese Early Opened Patent application Publication No. 50-123819 (Filing Date: Mar. 14, 1974; Inventor: Hideaki Manita et al; Applicant: Teikoku Zoki Seiyaku Kabushiki Kaisha; Date of Laying-Open: Sept. 29, 1975).

This second prior art publication discloses a method for immunological assay of steroids contained in human body fluid or excreted fluid which utilizes an antibody obtainable from a mammal immunized with steroid conjugated with antigenic protein having free amino group and sensitized carriers wherein carriers are sensitized with the steroid conjugated with protein which is different from the antigenic protein. In this second prior art method, adjustment of sensitivity can be achieved by varying the amount of the steroid-protein conjugate for sensitizing latex particles in the reagent and by varying the concentration of the antiserum. Though the descriptions in the second prior art publication are not necessarily clear, even if they may suggest that a smaller amount of excess antiserum can agglutinate sensitized latex particles when the latex particles are sensitized with a smaller amount of the steroid-protein conjugate, this approach may not give a significant improvement of sensitivity for the reason mentioned below. Originally, latex particles have a tendency to show non-specific agglutination when a proper stabilizing agent is not added thereto, and this non-specific agglutination cannot be distinguished from specific agglutination due to the antigen-antibody reaction. The steroid-protein conjugate used for sensitization of latex particles may act as a stabilizing agent for eliminating this non-specific agglutination of the latex particles proper. Accordingly the adjustment of sensitivity in the second prior art method is limited to a certain extent where non-specific agglutination is eliminated, and it is not possible to increase sensitivity beyond the limitation.

An approach to overcoming this limitation is considered to use the techniques disclosed in Japanese Patent Publication No. 49-11407 (Filing Date: Dec. 29, 1970; Inventor: Tadamitsu Sudo; Applicant: Teikoku Zoki Seiyaku Kabushiki Kaisha; Publication Date: Mar. 16, 1974) and Japanese Early Opened Patent application Publication No. 50-82230 (Filing Date: Nov. 29, 1973; Inventor: Tadamitsu Sudo et al; Applicant: Teikoku Zoki Seiyaku Kabushiki Kaisha; Date of Laying-Open: July 3, 1975). In these third and fourth prior art publications, it is disclosed that latex particles can be stabilized by making latex particles absorb an immunologically inert protein before or after the latex particles are sensitized with steroid-protein conjugate or antibody. Combining the second prior art publication and the third or fourth prior art publication, there is a possibility of obtaining sensitized latex particles having increased sensitivity with the latex particles being sensitized with a smaller amount of steroid-protein conjugate and being stabilized with an immunologically inert protein. It has been found, however, that this stabilization of latex particles by the inert protein tends to affect the immunologically specific agglutination.

Japanese Early Opened Patent application Publication No. 48-49918 (Filing Date: Oct. 26, 1972; Inventor: John Anthony Coppola et al; Applicant: American Cyanamid Company; Date of Laying-Open: July 14, 1973) discloses a method for preparation of antibody which has excellent specificity against progesterone and applicability of the antibody for radioimmunoassay and an agglutination test for determination of the concentration of progesterone in test samples. However, this fifth prior art publication does not generally refer to improvement of sensitivity for detection of a variety of steroids.

Moreover, in this fifth prior art publication, it is apparently stated that the steroid (hydroxyprogesterone)-protein conjugate has 15–40 molecules of steroid per molecule of protein, and this conjugate is used not only for preparation of antibody but also for sensitization of latex particles. Also, in the second prior art publication (Japanese Early Opened Patent application Publication No. 50-123819), estriol-16α-glucuronide—rabbit serum albumin conjugate is used for sensitization of latex particles, and the bonding ratio of steroid glucuronide to protein ranges from 27 to 30 moles per mole of protein used.

As will be seen from the foregoing, steroid-protein conjugates in which a relatively large number of molecules of steroid are bonded per molecule of protein have been used for sensitization of latex particles in the prior art (hereinafter the number of molecules of steroid which are bonded to a molecule of protein is simply referred to as the steroid bonding number).

The inventors have considered that further improvement of sensitivity would not be expected through conventional approaches, and the inventors' attempts have been concentrated on improvement of the conjugate proper. As a result, the inventors have found that when a steroid-serum albumin conjugate is prepared so that the steroid bonding number falls within a range of 0.5–7.0, and then latex particles are sensitized with such conjugate, the thus obtained sensitized latex particles show extremely high sensitivity, and that this is applicable irrespective of the sort of steroid and serum albumin used. As far as the inventors know, there is no reference which refers to decreasing steroid bonding number for increasing sensitivity of steroid detection.

SUMMARY OF THE INVENTION

Therefore, one of the primary objects of this invention is to provide a method for preparation of a latex polymer sensitized with steroid-serm albumin conjugate having increased steroid detection sensitivity in which the steroid for preparation of the conjugate is bonded to serum albumin in a ratio ranging from 0.5 to 7 mole to 1 mole of serum albumin.

Another object of this invention is to provide a method for preparation of a latex reagent which may detect steroids with a high sensitivity although the latex particles are sensitized only with steroid-serum albumin conjugate without stabilizing the latex particles with immunologically inert protein.

A further object of this invention is to provide a method for preparation of a polymer latex sensitized with steroid-serum albumin conjugate for detecting steroids with increased sensitivity wherein the latex polymer is selected from the group consisting of styrene polymer, butadiene polymer and styrene-butadiene copolymer.

A still further object of this invention is to provide a method for preparation of a latex polymer sensitized with steroid-serum albumin conjugate having increased steroid detection sensitivity wherein the steroid for preparation of the conjugate is selected from the group consisting of the steroid to be detected, metabolites thereof and synthetic steroids having similar structure thereto, and the serum albumin for preparation of the conjugate is selected from the group consisting of bovine serum albumin, equine serum albumin, sheep serum albumin, rabbit serum albumin and human serum albumin.

Another primary object of this invention is to provide a latex reagent having high sensitivity for steroid detection wherein latex particles are sensitized with steroid-serum albumin conjugate having a relatively small steroid bonding number.

These and other objects and features of this invention will become apparent with reference to the following detailed description of this invention.

DETAILED DESCRIPTION OF THE INVENTION

First the general and basic aspects of the present invention will be described and then discussion will enter into the details thereof.

Steroid

Generally speaking, steroids which can be utilized in the present invention are the following:
follicular hormone (estrogen),
corpus luteum hormone (progestrone),
male sex hormone (for example, 17-ketosteroid),
adrenocortical hormone (for example, 17-hydroxycorticosteroid), and
steroids which may be a variety of metabolites of the steroid hormones mentioned above These steroids when used for preparing conjugates with serum albumin are preferably in the states in which they are found in human body fluid or excreted fluid, for example in the state of steroid-glucuronide conjugates or steroid-sulphate conjugates.

However, any natural or synthesized steroids may be utilized provided they have sufficient immunological cross-reactivity with any specific steroid hormone or metabolite thereof to be detected in human body fluid or excreted fluid and provided they have a functional group in which they may be chemically bonded to serum albumin. For instance, steroid-hemisuccinate or steroid-(O-carboxymethyl)oxime may be utilized as a synthetic steroid.

Serum Albumin

Any refined serum albumin which is commercially available may be utilized, for example,

| | |
|---|---|
| Bovine Serum Albumin | (BSA) |
| Equine Serum Albumin | (ESA) |
| Sheep Serum Albumin | (SSA) |
| Rabbit Serum Albumin | (RSA) |
| Human Serum Albumin | (HSA) |

The codes shown in parentheses above are the initials of the respective serum albumins, and hereinafter these codes are utilized for simplicity.

Especially BSA or RSA is preferable among them.

Latex Particles

The following latex particles are commercially available and may conveniently be utilized in the present invention:

Polystyrene Latex Particles
Polybutadiene Latex Particles
Styrene-Butadiene Copolymer Latex Particles It is important that the latex particles do not have reactive radicals and they must be inert in the chemical and immunological senses. Polystyrene latex particles are especially preferable among them.

The particle size may be 0.05 $\mu$m–1.0 $\mu$m and preferably 0.2 $\mu$m–0.8 $\mu$m.

Preparation Of Conjugate

The following methods are known and may adequately be utilized in the present invention for preparing a steroid-serum albumin conjugate which is utilized for sensitizing latex particles and for obtaining antiserum or antibody.

Carbodiimide method (cf. Gross et al: Immunochemistry, Vol. 5, page 55, 1968),

Acid Chloride method (cf. Erlanger et al: Journal of Biological Chemistry, Vol. 228, page 713, 1957), Mixed Acid Anhydride method (ditto), and Isocyanate method (Goodfriend et al: Canadian Journal of Biochemistry and Physiology, Vol. 36, page 1177, 1958)

An example of preparation of steroid-serum albumin conjugate by the Mixed Acid Anhydride method is shown hereunder.

Ten moles of steroid-glucuronide, steroid-hemisuccinate or steriod-(O-carboxymethyl)oxime per mole of serum albumin to be used were dissolved in dimethylformamide. To this solution, the same number of moles of tri-n-butylamine as of the steroid were added as an auxiliary activator and the mixture was agitated. Then the same number of moles of isobutylchloroformate as of the steroid were further added as an activator to the thus obtained mixed solution and the mixture was agitated. The thus obtained mixed solution was referred to as liquid A.

On the other hand, serum albumin was dissolved in deionized water, and after adjusting its pH to 8.0–10.0 with N NaOH, dimethylformamide was added thereto. The thus obtained solution was referred to as liquid B. The quantity of dimethylformamide in liquid B was determined so that the total quantity of dimethylformamide in liquids A and B was the same as that of the deionized water in liquid B.

Then liquid A was added dropwise to liquid B over one and a half hours with agitation, and after its pH was adjusted to 8.0–10.0 with N NaOH, the mixed liquid was agitated for three and a half hours whereby steroid-serum albumin conjugate was synthesized. The thus obtained mixed liquid was dialyzed against water, and then acetone was added thereto in the ratio of two parts of acetone per one part of the dialyzed mixed liquid and they were homogeneously mixed. Adding N HCl to the mixed liquid to precipitate the conjugate, the precipitated conjugate was centrifugally separated. The proper quantity of water was added to the separated precipitate, and N NaOH was added thereto for adjusting its pH to 8. The thus obtained solution was subjected to dialysis against water for removing acetone whereby the conjugate was taken up. The process for preparation of the conjugate was carried out at low temperature (about 6° C.).

The steroid bonding number in the conjugate can be determined by known methods, for example, the ultraviolet absorption method and the dinitrophenylation method (see Test 1).

Sensitization Of Latex Particles

A suspension of latex particles was prepared by washing and/or diluting latex particles with a suitable buffer solution (pH 7.2–8.6), and the steroid-serum albumin conjugate which was prepared in a proper concentration was added thereto and the mixture was kept at 37° C. for 2 hours with agitation to obtain a suspension of sensitized latex particles. The suspension was centrifuged and the precipitate was separated, and then washed with the buffer solution. The centrifugation and washing were repeated several times, and the thus obtained precipitate was resuspended in the buffer solution to obtain a suspension of latex particles sensitized with the conjugate. The quantity of the conjugate utilized for sensitizing the latex particles may be limited within a range within which the following requirements are fulfilled:

(1) The sensitized latex particles finally obtained do not show non-specific agglutination due to the nature of the latex particles proper.

(2) Specific agglutination due to the antigen-antibody reaction can occur.

(3) When antibody is neutralized with a sufficient amount of steroid hapten and then the suspension of the sensitized latex particles is added thereto, the resulting mixed liquid remains a homogeneous suspension without any agglutination.

As will be mentioned hereunder, the amount of conjugate used for sensitization of latex particles (hereinafter referred to as the sensitizing quantity) is varied depending on the size of the latex particles and the steroid bonding number in the conjugate to be used.

Latex particles having different sizes, 0.234 $\mu$m and 0.721 $\mu$m were respectively sensitized with a conjugate in which estriol-16$\alpha$-glucuronide was bonded to RSA in the ratio of 2.0 molecules per molecule of RSA in accordance with the process mentioned above. The minimum sensitizing quantities in the respective latex particles for eliminating non-specific agglutination were 72 mg and 18 mg per gram of latex particles. In general the smaller particles tend to require larger sensitizing quantities.

Latex particles having a particle size of 0.234 $\mu$m were sensitized with estriol-16$\alpha$-glucuronide conjugate having a steroid bonding number of 15.1 using different sensitizing quantities. The minimum sensitizing quantity for eliminating non-specific agglutination was 54 mg per gram of the latex particles. It should be noted that the minimum sensitizing quantity in the latter case was relatively small compared with that in the former case (72 mg/g) in which latex particles were sensitized with the conjugate having a steroid bonding number of 2.0 (see Table 1).

It should also be noted that sensitization of latex particles can be performed by dialysis, ultrafiltration or combination of any one of them with the aforementioned method. Also sensitized latex particles can be freeze dried.

Preparation Of Antibody

Antibody may be prepared by conventional methods, for example, antiserum or antibody separated therefrom may be obtainable in such a manner that steroid-serum albumin conjugate is first prepared by reacting steroid in the state found in human body fluid or excreted fluid, or steroid having immunological cross-reactivity therewith, to serum albumin, and then the thus obtained conjugate is non-orally dosed (e.g. injected) to a mammal which has serum foreign to the serum used to prepare the conjugate for immunizing the mammal from which antiserum is to be collected. Antiserum thus obtained may be utilized as original antibody. Of course, the antibody may be separated from the antiserum.

It should be noted that the steroid to be detected may react as a hapten with the antibody, and the conjugate for sensitizing the latex particles also may react therewith.

Steroid Detection

The conventional method is utilized except that latex reagent prepared in accordance with the present invention is used. The detection method comprises the following two processes:

(1) A given quantity of human body fluid or excreted fluid either undiluted or properly diluted is taken out as a test sample, and a given quantity of antibody is added and mixed with the test sample to produce an antigen-antibody reaction between the steroid which is the hapten contained in the test sample and the antibody (neutralization of antibody).

(2) A given quantity of the mixture of the test sample and the antibody is dropped on a glass slide and a given quantity of the latex reagent is added thereto and mixed with an elongated small rod, and the mixed liquid on the glass slide is observed a few minutes later to determine whether an agglutination reaction has occurred or not.

That is, if the antibody is not fully neutralized by the steroid contained in the test sample and consequently an excess amount of the antibody remains after the first process, then antigen-antibody reaction occurs between the latex reagent and the remaining antibody and agglutination can be observed in the second process. In case the antibody is fully neutralized with the steroid contained in the test sample (including the case in which an excess amount of steroid remains in the first process), no antigen-antibody reaction occurs and agglutination cannot be observed, that is, agglutination inhibition reaction is observed in the second process.

It will be understood that the concentration of the test samples, latex reagent and the antibody can be properly determined depending upon the anticipated or reference concentration of steroid hormone and/or its metabolite to be tested in the test sample. The agglutination reaction in the second process may be terminated at the latest within 5 minutes.

Having described the general and basic aspects of the latex reagent, method for preparation thereof and the method for detecting steroids using the latex reagent in accordance with the present invention, now the invention will be further described in detail based on a number of exemplifying tests and examples of the present invention.

TEST 1

I. Material Preparation (1) Conjugate Preparation

Using estriol-16α-glucuronide (Sigma Company) and RSA (INC Pharmaceuticals Company), nine kinds of conjugate which were different in steroid bonding number were prepared as follows:

Liquid A Preparation

Ten milligrams of estriol-16α-glucuronide were dissolved in 1 ml of dimethylformamide (Wako Junyaku Kogyo Kabushiki Kaisha). To this solution, 5.1 $\mu$l of tri-n-butylamine (Tokyo Kasei Kogyo Kabushiki Kaisha) were added and the solution was agitated. Then, 2.8 $\mu$l of isobutylchloroformate (Aldrich Chemical Company) were added and the solution was agitated.

The same quantity of liquid A was prepared in 9 vessels.

Liquid B Preparation

RSA was dissolved in deionized water as shown in Table 3 to obtain RSA solutions having different concentrations. Adding N NaOH to the respective solutions, the pH was adjusted to 8.0–10.0. To these solutions different amounts of dimethylformamide were added, and 9 kinds of liquid B in which different amounts of RSA were contained were prepared. The amount of dimethylformamide contained in each of liquids B was adjusted so that the total amount of dimethylformamide contained in liquids A and B was equal to the amount of deionized water contained in liquid B.

Conjugate Preparation

One sample of liquid A was added dropwise to each sample of the liquid B over one and a half hours with agitation, by adding N NaOH to the respective solutions the pH was adjusted to 8.0–10.0, and each of these solutions was further agitated for 3 hours. Thus and 9 kinds of estriol-16α-glucuronide-RSA conjugate solutions were obtained.

Each of these solutions was subjected to dialysis against deionized water. To the dialyzed solutions acetone was respectively added in the ratio of 2 parts acetone per 1 part of the solution, and after suficient agitation N HCl was respectively added to precipitate the conjugate. The precipitated conjugate in each of the solutions was separated by centrifugation for 5 minutes at 10,000 r.p.m. To each of the separated conjugates deionized water was added, and after adjusting its pH to about 8 with N NaOH, each of these solutions was dialyzed against deionized water to remove acetone. Thus 9 kinds of conjugates having different steroid bonding numbers (see Table 3, Samples Nos. 1–9) were obtained. The processes of preparation of the conjugate were carried out at low temperature (6° C.).

The respective steroid bonding numbers in the conjugates are shown in Table 3. Measurement of steroid bonding number will be described later on.

Conjugate Latex Particles Preparation

Minimum sensitizing quantities with respect to the conjugates of samples Nos. 1–9 for eliminating non-specific agglutination of the obtainable conjugate latex particles were determined as follows:

Dissolving 5.0, 5.2, 5.4 and 5.6 mg of sample No. 1 (conjugate) in Table 3 respectively in 40 ml of 40 mM veronal buffer solution containing 150 mM NaCl, 4 kinds of conjugate solutions were prepared. Then each of the 4 kinds of conjugate solutions, 1 ml of a 10% suspension of the latex particles (Dow Chemical Co.) having a particle size of 0.234 μm was added, and they were kept at 37° C. for 2 hours. The thus obtained sensitized latex particle suspensions were each subjected to centrifugation at 4,000 r.p.m. for 20 minutes to precipitate the sensitized latex particles. The separated precipitates were each suspended in 20 ml of the same veronal buffer solution and were centrifuged under the same condition mentioned above to separate the sensitized latex particles. This last mentioned process was respectively repeated once again, and the thus obtained precipitates were each resuspended in 5 ml of the same veronal buffer solution, and 4 kinds of sensitized latex particle suspensions having different sensitizing quantities were thus obtained.

On glass slides, 0.1 ml of each of the sensitized latex particle suspensions was respectively dropped to which 0.1 ml of the antiserum which was neutralized with an excess amount of estriol-16α-glucuronide was respectively added and mixed. Several minutes later, the presence of non-specific agglutination in the respective mixed drops was observed.

Non-specific agglutination was observed in the droplets for the conjugate sensitized latex particle suspensions having sensitizing quantities of 5.0 mg and 5.2 mg of the sample No. 1, and was not observed in those prepared using 5.4 mg and 5.6 mg of sample No. 1. Thus the minimum sensitizing quantity of sample No. 1 was determined as 5.4 mg per 0.1 g of latex particles.

Like tests were conducted with respect to samples No. 2–No. 9 to determine the respective minimum sensitizing quantities. The results are shown in Table 1.

TABLE 1

| Sample No. | 1 | 2 | 3 | 4 | 5 | 6 | 7 | 8 | 9 |
|---|---|---|---|---|---|---|---|---|---|
| estriol-16α-glucuronide bonding number (per 1 molecule of RSA) | 15.1 | 10.7 | 7.4 | 5.1 | 3.2 | 2.0 | 0.9 | 0.5 | 0.3 |
| minimum sensitizing quantity (mg/0.1 g latex particles) | 5.4 | 5.9 | 6.3 | 6.5 | 7.0 | 7.2 | 7.4 | 7.4 | 7.4 |

Using the respective minimum sensitizing quantities of the samples No. 1–No. 9, sensitized latex particle suspensions of the samples No. 1–No. 9 were respectively prepared.

II. Measurement of Steroid Bonding Number and Steroid Detection Sensitivity (1) Steroid Bonding Number Measurement Steroid bonding number measurement was carried out by the method of Erlanger et al utilizing ultraviolet absorption (Journal of Biological Chemistry, Vol. 234, page 1090, 1959) and by Sanger's method utilizing dinitrophenylation (Biochemical Journal, Vol. 39, page 507, 1945).

(i) Measurement by Ultraviolet Absorption

Estriol-16α-glucuronide and RSA absorb in the same spectral region, i.e., with a maximum at 278 nm, and the absorption maximum of the conjugate thereof can be measured as the sum of the absorption maxima of the respective components. Accordingly the absorbance derived from estriol-16α-glucuronide in the conjugate can be obtained by subtracting the absorbance of RSA from that of the conjugate. Comparing the thus obtained absorbance derived from estriol-16α-glucuronide in the conjugate with the absorbances of a variety known concentrations of estriol-16α-glucuronide, the estriol-16α-glucuronide bonding number was obtained.

(ii) Measurement by Dinitrophenylation

Lysine radicals (Lys) in the conjugate and in the serum albumin used for preparing the conjugate were respectively dinitrophenylated with dinitrofluorobenzene (Wako Junyaku Kogyo Kabushiki Kaisha) to produce dinitrophenylated conjugate and dinitrophenylated serum albumin. Then these dinitrophenylated products were respectively hydrolyzed at 110° C. to obtain 24 hours for free dinitrophenyllysine. Thus two kinds of solutions containing dinitrophenyllysine were obtained, one derived from the conjugate and the other derived from serum albumin. On the other hand, commercially available dinitrophenyllysine (Tokyo Kasei Kogyo Kabushiki Kaisha) was obtained as a reference substance and serially diluted solutions thereof were prepared. The former two kinds of dinitrophenyllysine containing solutions and serially diluted reference dinitrophenyllysine solutions, were subjected to colorimetric determination at 390 nm, and the steroid bonding number in the conjugate was calculated from the values of the optical density thereof.

(2) Measurement of Steroid Detection Sensitivity

In general, steroid detection sensitivity was measured in such a manner that first the titer of the original antibody was determined with reference steroid solution, and then the titer of the respective samples No. 1–No. 9 was determined with reference to the titer of the original antibody. The details thereof are mentioned below.

(i) Determination of Titer of Antibody

Antiserum was obtained from rabbits which were immunized with estriol-16α-glucuronide-BSA conjugate by a proper conventional method, and the antiserum was utilized as an original antibody. This original antibody was serially diluted with 40 mM veronal buffer solution containing 150 mM NaCl. To 0.05 ml of the serially diluted antibody, 0.05 ml of a solution prepared by dissolving 0.1 nmole of estriol-16α-glucuronide per 1 ml of the buffer solution was respectively added and agitated well. Taking dropwise 0.1 ml of the respective agitated mixed solutions on glass slides, 0.1 ml of the conjugate sensitized latex particle suspension having an estriol-16α-glucuronide bonding number of 2.0 was added to each of the droplets on the glass slides and they were agitated well. Observation after 3 minutes showed that agglutination reaction was detectable in the droplets having 200-fold or less dilution of the original antibody.

TABLE 2

| Dilution of antibody | ×50 | ×100 | ×200 | ×300 | ×400 |
|---|---|---|---|---|---|
| Agglutination | + | + | + | − | − |

This means that the original antibody when diluted 200-fold can neutralize at least 0.1 nmole of estriol-16α-glucoronide/ml.

Thus the titer of this 200-fold antibody was determined to be 0.1 nmole estriol-16α-glucoronide equivalent/ml, and the titer of the original antibody to be 20 nmole estriol-16α-glucoronide equivalent/ml.

(ii) Determination of Titer of Latex Reagent

The original antibody was serially diluted with 40 mM veronal buffer solution and 0.1 ml of each of the serially diluted antibody samples was dropped on glass slides. To these droplets 0.1 ml of each of the samples No. 1–No. 9 (see Table 1) was added and agitated well, and the results were observed after 3 minutes. Based on the maximum dilution in the droplets in which agglutination reaction was observed and the titer of the original antibody, the titers of the latex reagent samples were calculated. It will be understood therefore that a smaller numerical value of the titer means higher detection sensitivity.

The estriol-16α-glucoronide bonding number and detection sensitivity of respective samples No. 1–No. 9 are shown in Table 3.

TABLE 3

| | preparation condition | | | Estriol-16α-glucoronide bonding number | | detection sensitivity Estriol-16α-glucoronide |
| --- | --- | --- | --- | --- | --- | --- |
| sample No. | RSA (mg) | Estriol-16α-glucoronide/RSA (mole ratio) | deionized water (ml) | ultraviolet absorption method | dinitro-phenylation method | equivalent antibody (nmole/ml) |
| 1 | 56 | 25.0 | 1.4 | 15.1 | 17.2 | 1.60 |
| 2 | 93 | 15.0 | 2.4 | 10.7 | 11.9 | 0.53 |
| 3 | 140 | 10.0 | 3.0 | 7.4 | 8.7 | 0.13 |
| 4 | 200 | 7.0 | 5.1 | 6.2 | | 0.09 |
| 5 | 311 | 4.5 | 8.0 | 3.2 | 3.6 | 0.05 |
| 6 | 466 | 3.0 | 12.0 | 2.0 | 2.4 | 0.04 |
| 7 | 932 | 1.5 | 24.0 | 0.9 | 1.5 | 0.05 |
| 8 | 1863 | 0.75 | 48.0 | 0.5 | 0.7 | 0.08 |
| 9 | 2795 | 0.5 | 72.0 | 0.3 | 0.5 | 0.19 |

From this Table 3, it will be noticed that there is a correlation between the steroid bonding number and the detection sensitivity of the samples No. 1–No. 9. That is, detection sensitivity increases as steroid bonding number decreases. However, detection sensitivity reaches the maximum when the steroid bonding number is 2.0 (by the ultraviolet absorption method), and thereafter detection sensitivity decreases as steroid bonding number decreases.

Therefore, it will be understood that in accordance with the present invention excellent sensitivity, over 0.2 nmole estriol-16α-glucoronide equivalent/ml, is achieved, and it is remarkably higher than that of the conventional latex reagent which is at the level of 2.5 nmole estriol-16α-glucoronide equivalent/ml.

This excellent detection sensitivity may be obtained when the steroid bonding number falls within a range of about 0.5–8.7 measured by both the ultraviolet absorption method and the dinitrophenylation method. Higher sensitivity, over 0.1 nmole estriol-16α-glucoronide equivalent/ml, may be achieved when the steroid bonding number falls within a range 0.7–7.0.

TEST 2

A test similar to Test 1 was conducted with respect to latex particles sensitized with dehydroepiandrosterone-17-(O-carboxymethyl)oxime-BSA conjugate.

Using dehydroepiandrosterone (Sigma Company) (hereinafter referred to DHEA) and BSA (ICN Pharmaceuticals Company), 8 kinds of conjugates having different steroid bonding numbers within the range 0.5–18.3 were prepared as follows:

Amounts of 0.75 g of DHEA and 0.69 g of (O-carboxymethyl) hydroxylamine hydrochloride (Wako Junyaku Kogyo Kabushiki Kaisha) were dissolved in 20 ml of ethyl alcohol.

In 20 ml of ethyl alcohol, 0.75 g of DHEA and 0.69 g of (O-carboxymethyl)hydroxylamine hydrochloride (Wako Junyaku Kogyo Kabushiki Kaisha) were dissolved and 2 ml of 6.4 M sodium succinate solution added thereto to keep it alkaline. The resulting solution was refluxed for an hour to promote the reaction, and then $Na_2CO_3$ was added thereto. The quantity of $NaCO_3$ to be added was such that the concentration of $Na_2CO_3$ in the resulting solution amounted to 5%.

After wahing the resulting solution with ether, its aqueous layer was acidified with concentrated hydrochloric acid and the resulting precipitate was separated. This precipitation was recrystallized from ethyl alcohol and 0.6 g of DHEA-17-(O-carboxymethyl)oxime (hereinafter referred to DHEA-CMO) was obtained.

Using this DHEA-CMO and BSA in the mole ratios shown in Table 4, 8 kinds of conjugate (samples No. 1–No. 8) having different steroid bonding numbers were prepared in like manner as in Test 1. The steroid bonding number in the samples No. 1–No. 8 was measured by the dinitrophenylation method. The results are also shown in Table 4.

The minimum sensitizing quantity was determined with respect to the samples No. 1–No. 8 in like manner as in Test 1. The results are also shown in Table 4.

Using the minimum sensitizing quantity of samples No. 1–No. 8, 8 kinds of latex reagents were prepared and the steroid detection sensitivity was measured with respect to these samples as follows:

To 1 ml of a 10% suspension of latex particles (Dow Chemical Company) having a particle size of 0.721 μm, 4 ml of 20 mM phosphoric acid buffer solution (pH 7.2) containing 150 mM NaCl was added. After sufficient agitation, the resulting solution was centrifuged at 4,000 r.p.m. for 20 minutes. The obtained precipitate was suspended in 5 ml of the same buffer solution. The resulting suspension was centrifuged again under the same conditions mentioned above and the precipitate was separated. The same quantity of such washed latex particles was prepared in 8 lots.

The minimum sensitizing quantities of the respective conjugate samples No. 1–No. 8 in Table 4 were dissolved in 5 ml of the buffer solution to prepare 8 kinds of conjugate solutions having different steroid bonding numbers, and these solutions were respectively added to the 8 lots of said washed latex particles. After keeping the resulting solutions at 37° C. for 2 hours, they were each subjected to centrifugation and washing with the buffer solution twice. The resulting precipitates were each resuspended in 5 ml of the buffer solution and thus were obtained 8 kinds of DHEA-CMO-BSA sensitized latex particle suspensions (Table 4, samples No. 1–No. 8).

Meanwhile antiserum was obtained from rabbits immunized with DHEA-CMO-ESA, and this was utilized as an original antibody. The original antibody was serially diluted with 20 mM phosphoric acid buffer solution (pH 7.2) containing 150 mM NaCl. An amount of 0.05 ml of each of the diluted antibody, solutions was respectively mixed with 0.05 ml of a solution prepared by dissolving 0.2 nmole of DHEA per ml of the buffer solution to neutralize the antibody therein. On glass slides, 0.1 ml of each of the respective neutralized solutions was dropped and to each of these droplets 0.1 ml of a suspension of latex particles sensitized with the conjugate having a DHEA bonding number of 2.4 was respectively added and agitated well. Maximum dilution of antibody which enabled detection of agglutination within 3 minutes was 50-fold. Therefore the titer of 50-fold diluted antibody was determined as 0.2 nmole DHEA equivalent/ml and the titer of the original antibody as 10 nmole DHEA equivalent/ml.

Next, the original antibody was serially diluted with 20 mM phosphoric acid buffer solution, and 0.1 ml of each of the diluted antibody solutions was respectively mixed with 0.1 ml of the latex reagent samples No. 1–No. 8 on glass slides, and the maximum dilution of the antibody which gave agglutination within 3 minutes was determined. Respective detection sensitivities of latex reagent samples No. 1–No. 8 were calculated in like manner as in Test 1 based on the maximum dilution and the titer of the original antibody. The calculated titers are also shown in Table 4.

TABLE 4

| sample No. | preparation condition BSA (mg) | preparation condition DHEA-CMO/BSA (mole ratio) | DHEA bonding number dinitro-phenylation method | DHEA-CMO-ESA sensitizing quantity (mg/0.1 g latex particles) | detection sensitivity Estriol-16α-glucuronide equivalent antibody (nmole/ml) |
|---|---|---|---|---|---|
| 1 | 71.9 | 25.0 | 18.3 | 1.2 | 1.40 |
| 2 | 120 | 15.0 | 11.0 | 1.3 | 0.50 |
| 3 | 180 | 10.0 | 7.7 | 1.3 | 0.15 |
| 4 | 257 | 7.0 | 5.6 | 1.5 | 0.10 |
| 5 | 400 | 4.5 | 3.6 | 1.7 | 0.07 |
| 6 | 600 | 3.0 | 2.4 | 1.7 | 0.05 |
| 7 | 1200 | 1.5 | 1.2 | 1.8 | 0.05 |
| 8 | 2400 | 0.75 | 0.5 | 1.8 | 0.08 |

From Table 4, it will be seen that the highest sensitivity is obtained when the DHEA-CMO bonding number falls within the range of 1.2–2.4, and sensitivity over 0.2 nmole DHEA equivalent/ml is obtained when the DHEA-CMO bonding number falls within the range of 0.5–7.7.

TEST 3

Using various kinds of steroids and serum albumins which were not used in Tests 1 and 2, similar tests were conducted. The maximum and minimum values of steroid bonding number with which higher sensitivity over 0.2 nmole steroid equivalent/ml is obtainable are shown in Table 5.

TABLE 5

| conjugate for sensitizing latex particles | steroid bonding number minimum | steroid bonding number maximum |
|---|---|---|
| progesterone-11-hemisuccinate-RSA | 0.5 | 8.0 |
| hydrocortisone-21-hemisuccinate-HSA | 0.5 | 7.0 |
| aldosterone-3-(o-carboxymethyl)oxime-ESA | 0.5 | 7.5 |
| testosterone-17-glucoronide-RSA | 0.5 | 8.6 |
| pregnanediol-3-hemisuccinate-ESA | 0.5 | 7.3 |

From the foregoing it has been found that regardless of steroid and serum albumin used higher sensitivity over 0.2 nmole steroid equivalent/ml is obtained when the steroid bonding number of the conjugate falls within the range 0.5–7.0.

TEST 4

A comparative test for steroid detection sensitivity between the latex reagent prepared in accordance with the present invention and that prepared by the conventional method was conducted as follows:

Latex reagent by the conventional method was prepared in the same manner as in Test 1 except that 47 mg of RSA (ICN Pharmaceuticals Company) and 1.0 ml of deionized water were used, and estriol-16α-glucuronide-RSA conjugate was obtained. The steroid bonding number in this conjugate was 20 by the ultraviolet absorption method referred to in Test 1. Using different quantities of this conjugate, latex particles were sensitized in like manner as in Test 1 and differently sensitized latex reagents so obtained were subjected to a stability test for non-specific agglutination in like manner as in Test 1. The minimum sensitizing quantity of the conjugate for eliminating non-specific agglutination was determined to be 5.0 mg per 0.1 g of latex particles.

Thus a comparative latex reagent (sample No. 10) was prepared by sensitizing latex particles with the minimum sensitizing quantity of the conjugate.

Furthermore additional comparative latex reagents (samples Nos. 11–14) were prepared in such a manner that latex particles were sensitized with the minimum quantities of the conjugates which were differently modified from that used for sample No. 10. More specifically the conjugate was modified in such a manner that to the same quantity of the conjugate prepared in 4 lots, different quantities of an aqueous solution of immunologically inert RSA were respectively added so that the resultant mole ratio of the steroid to the total RSA in the modified conjugates came to be 1, 2, 5 and 10, and then with respect to these modified conjugates the maximum sensitizing quantities were determined in like manner as in the foregoing tests. Then using the respective minimum sensitizing quantities of the 4 kinds of modified conjugates, latex particles were sensitized and the additional comparative latex reagents (samples Nos. 11–14) were prepared.

Using the thus obtained 5 kinds of comparative latex reagent samples Nos. 10–14 and the latex reagent samples Nos. 6 and 9 in Test 1, a comparative test for steroid detection sensitivity was conducted in like manner as in Test 1. The results are shown in Table 6.

TABLE 6

| sample No. | mixing ratio of inert RSA and sample No. 10 (RSA: sample No. 10) | steroid bonding number (per 1 molecule of total RSA) | sensitizing quantity (mg/0.1 g latex particles) | detection sensitivity Estriol-16α-glucuronide equivalent antibody (nmole/ml) |
|---|---|---|---|---|
| 6* | — | 2.0 | 7.2 | 0.04 |
| 9* | — | 0.3 | 7.4 | 0.19 |
| 10 | — | 20 | 5.0 | 2.5 |
| 11 | 1 : 1 | 10 | 6.0 | 1.5 |
| 12 | 3 : 1 | 5 | 6.7 | 1.0 |
| 13 | 9 : 1 | 2 | 7.4 | 0.5 |
| 14 | 19 : 1 | 1 | 7.5 | 0.8 |

(Note)
*latex particles sensitized with the conjugate in accordance with the present invention From Table 6, it will be noted that the steroid detection sensitivity of sample No. 6 is 62.5 times that of sample No. 10, and that sensitivity of the sample No. 9 is 13 times that of sample No. 10 though sample No. 9 has the lowest sensitivity among the samples of the present invention. Therefore, it is clear that the latex reagents of this invention have much higher sensitivity than the conventional latex reagent which has rather large steroid bonding number.

Regarding additional comparative latex reagent samples Nos. 11–14, the steroid detection sensitivity of the sample No. 13 is the highest among them, but the sensitivity is almost 1/12 of that in the sample No. 6 and about 2/5 of that in the sample No. 9. Furthermore though these reagent samples Nos. 11–14 have considerably small steroid bonding numbers comparable to those in the applicant's reagent samples, these reagent samples Nos. 11–14 are not necessarily considered to be conventional reagents, since there has been no reference, as far as the inventors know, which may teach or suggest decreasing the steroid bonding number to such a level for increasing sensitivity. In any case, it will be clear that the sensitivities of the samples Nos. 11–14 are not comparable to those in the samples of the present invention.

Therefore it will be understood that the present invention enables one to detect smaller concentrations of steroid which may not be detected with the conventional latex reagent, or alternatively to dilute a liquid to be tested for eliminating interference of coexisting substances when the liquid contains steroids in higher concentration. In other words the present invention makes possible more reliable quantitative assay of steroids and also more accurate diagnostic information.

Furthermore the present invention may provide a latex reagent having excellent high sensitivity, and therefore steroid detection can be achieved with lesser amounts of antibody or antiserum. Consequently this makes it possible to reduce consumption of antibody, and since preparation of antibody or antiserum involves very high cost the present invention is highly advantageous in from an economic point of view.

Having described exemplifying tests of the present invention, some examples of the present invention will be described for better understanding.

EXAMPLE 1

Liquid A was prepared by dissolving 50 mg of estriol-16α-glucuronide (Sigma Company) in 10 ml of dimethylformamide (Wako Junyaku Kogyo Kabushiki Kaisha), then 26 μl of tri-n-butylamine (Tokyo Kasei Kogyo Kabushiki Kaisha) and then 14 μl of isobutylchloroformate (Aldrich Chemical Company) were respectively added and agitated well.

On the other hand 2.33 g of RSA (ICN Pharmaceuticals Company) was dissolved in 60 ml of deionized water, 1.0 ml of N NaOH was added and thereafter 50 ml of dimethylformamide was added thereto whereby liquid B was prepared.

To this liquid B, previously prepared liquid A was added dropwise and agitated for an hour, then 0.1 ml of N NaOH was added and the mixture was further agitated for 3 and a half hours. After dialyzing the solution against deionized water, two parts of acetone were added per one part of the solution, and after thorough agitation N HCl was added to precipitate synthesized estriol-16α-glucuronide-RSA conjugate. The precipitate was separated by centrifugation at 10,000 r.p.m. for 5 minutes.

To the separated precipitate, deionized water was added and its pH was adjusted to 8 with N NaOH and then subjected to dialysis against deionized water to remove acetone. Thus 1.78 g of the conjugate was obtained (yield 75%). These processes were carried out at low temperature (6° C.). The steroid (estriol-16α-glucuronide) bonding number measured by the ultraviolet absorption method and dinitrophenylation method was 2.2 and 1.9 respectively.

Then 76 mg of the conjugate was dissolved in 400 ml of 40 mM veronal buffer solution (containing 150 mM NaCl, pH 7.8), and further 10 ml of polystyrene latex particle (particle size 0.234 μm) suspension (10% concentration) was added and kept at 37° C. for 2 hours for sensitization. The sensitized latex suspension was subjected to centrifugation at 4,000 r.p.m. for 20 minutes, and the obtained precipitate was suspended in 200 ml of the twice said buffer solution and then subjected to centrifugation under the same conditions mentioned above. The thus obtained precipitate was resuspended in 50 ml of the buffer solution, and then sodium azide was added so that the resultant concentration thereof came to be 0.1% whereby 50 ml of estriol-16α-glucuronide-RSA sensitized latex particle suspension (2% density) was obtained.

Mixing on a glass slide 0.1 ml of the thus obtained sensitized latex particle suspension and 0.1 ml of diluted anti estriol-16α-glucuronide-BSA antibody solution which was prepared in like manner as in Test 1 and diluted to have a titer of 0.04 nmole estriol-16α-glucuronide equivalent/ml, agglutination was observed within 1-2 minutes. However, when the antibody was diluted to have a titer of 0.02 n mole estriol-16α-glucuronide equivalent/ml, no agglutination was observed, and the titer of the latex reagent obtained in this example was determined to be 0.04 nmole estriol-16α-glucuronide equivalent/ml.

EXAMPLE 2

DHEA-CMO was prepared in like manner as in Test 2. Liquid A was prepared by adding 0.5 g of DHEA-CMO to 100 ml of dimethylformamide (Wako Junyaku Kogyo Kabushiki Kaisha), then 0.33 ml of tri-n-butylamine (Tokyo Kasei Kogyo Kabushiki Kaisha) was added, and further 0.18 ml of isobutylchloroformate (Aldrich Chemical Company) was added and the mixture was agitated well.

Meanwhile 18.0 g of BSA (Sigma Company) was added to 600 ml of deionized water and further 500 ml of dimethylformamide was added and thus liquid B was obtained.

To this liquid B, previously prepared liquid A was added dropwise, and after agitation for one and a half hours its pH was adjusted to 9.0 with N NaOH and the mixture further agitated for 3 and a half hours. The thus obtained solution was dialyzed against flowing water, then two parts of acetone were added per 1 part of the solution. After thorough agitation N HCl was added to the solution to precipitate the synthesized conjugate, and then the solution was subjected to centrifugation at 5,000 r.p.m. for 20 minutes. To the separated precipitate, deionized water was added, and after its pH was adjusted to about 8 with N NaOH, the solution was dialyzed against flowing water to remove acetone whereby 13.0 g of DHEA-CMO-BSA conjugate was obtained (yield about 70%). The steroid (DHEA-CMO) bonding number of this conjugate measured by the dinitrophenylation method was 4.1.

Then 68 mg of the thus obtained conjugate was dissolved in 100 ml of 100 mM glycine buffer solution (containing 130 mM NaCl and 0.1% of sodium azide, pH 8.2), and to this solution 10 ml of a 10% concentration suspension of polystyrene latex particles (Dow Chemical Company) was added, and then the mixture was dialyzed against said buffer solution at room temperature for 5 days for sensitization. The thus obtained sensitized latex suspension was subjected to centrifugation at 4,000 r.p.m. for 20 minutes, and after the precipitate was suspended in 200 ml of said buffer solution the suspension was twice subjected to centrifugation and washing with said buffer solution under the same conditions. Finally resuspending the obtained precipitate in 50 ml of said buffer solution, 50 ml of 2% concentration DHEA-CMO-BSA sensitized latex particle suspension was obtained.

Mixing on a glass slide 0.05 ml of 0.1 nmole/ml DHEA with 0.05 ml of diluted antibody which was prepared in like manner as in Test 2 and diluted with said buffer solution to have a titer of 0.1 nmole DHEA equivalent/ml, and then adding 0.1 ml of the eventually obtained sensitized latex particle suspension thereto, no agglutination was observed even after 10 minutes. When 0.1 ml of the sensitized latex particle suspension was added to the mixture of 0.05 ml of 0.02 nmole/ml DHEA and 0.05 ml of said diluted antibody, agglutination was observed within 2-3 minutes. Through a procedure similar to that of Test 1, the titer of the latex reagent obtained in this example was determined to be 0.05 nmole DHEA equivalent/ml.

EXAMPLE 3

Liquid A was prepared by dissolving 1.1 g of testosterone-17-glucuronide (Sigma Company) in 200 ml of dimethylformamide (Wako Junyaku Kogyo Kabushiki Kaisha), and to the thus obtained solution 0.52 ml of tri-n-butylamine (Tokyo Kasei Kogyo Kabushiki Kaisha) and then 0.28 ml of isobutylchloroformate (Aldrich Chemical Company) were successively added and the mixture was agitated well.

Liquid B was prepared by dissolving 46.6 g of RSA (Sigma Company) in 1.2 l of deionized water, and after its pH was adjusted to 9.0 with N NaOH, 1.0 l of dimethylformamide was added thereto. In like manner as in Example 2, about 39.0 g of testosterone-17-glucuronide-RSA (hereinafter referred to as T-17-G-RSA) was obtained (yield about 82%). The steroid (T-17-G) bonding number in this conjugate measured by the ultraviolet absorption method and the dinitrophenylation method was 2.3 and 2.1 respectively.

Then 400 ml of 20 mM phosphoric acid buffer solution containing 150 mM NaCl (pH 7.2) was added to 100 ml of a 10% concentration suspension of a polystyrene latex particles (Dow Chemical Company) having a particle size of 0.721 μm, then the suspension was subjected to centrifugation at 4,000 r.p.m. for 20 minutes. The thus obtained precipitate was suspended in 500 ml of said buffer solution and then centrifuging the suspension under the same conditions mentioned above, a precipitate was separated. Then 500 ml of said buffer solution containing 180 mg of the previously obtained conjugate were added to the separated precipitate. After the thus obtained suspension was kept at 37° C. for two hours, the suspension was subjected to centrifugation under the same conditions, and then washed with said buffer solution and the centrifugation process was repeated twice. The precipitation obtained was resuspended in 500 ml of said buffer solution, and finally sodium azide was added so that the eventual concentration thereof came to be 0.1%. Thus 500 ml of 2% concentration of T-17-G-RSA sensitized latex particle suspension was obtained.

In like manner as in Test 1, anti T-17-G-RSA antibody was prepared, and then it was diluted with said buffer solution to give a titer of 0.05 nmole T-17-G equivalent/ml. On a slide 0.1 ml of this diluted antibody was mixed with 0.1 ml of the eventually obtained latex particle suspension, and agglutination was observed within 1-2 minutes. However, when the antibody was diluted to give a titer of 0.02 nmole T-17-G equivalent/ml, no agglutination was observed within 5 minutes. Thus the latex reagent obtained in this example was determined to be 0.05 nmole T-17-G equivalent/ml.

EXAMPLE 4

Liquid A was prepared by adding a certain number of moles of sodiumhydrocortisone-21-hemisuccinate (Sigma Company) to the same number of moles of concentrated hydrochloric acid, and then concentrating and washing with water, and these concentration and washing processes were repeated several times and then the solution was evaporated to dryness, and 0.5 g of the thus obtained dried material was dissolved in 100 ml of dimethylformamide (Wako Junyaku Kogyo Kabushiki Kaisha), and successively 0.26 ml of tri-n-butylamine (Tokyo Kasei Kogyo Kabushiki Kaihsa) and 0.14 ml of isobutylchloroformate (Aldrich Chemical Company).

Meanwhile liquid B was prepared by dissolving 17.6 g of HSA (Miles Laboratories Inc.) in 600 ml of deionized water, and adjusting its pH to 9.0 with N NaOH and finally adding 500 ml of dimethylformamide. Thereafter, in like manner as in Example 2, about 13.6 g of hydrocortisone-21-hemisuccinate-HSA (hereinafter referred to as HC-21-HS-HSA) was obtained (yield about 75%). The steroid (HC-21-HS) bonding number in this conjugate measured by the dinitrophenylation method was 3.0.

Then 200 ml of 40 mM veronal buffer solution containing 150 mM NaCl (pH 7.8) was added to 50 ml of a 10% concentration suspension of polystyrene latex particles (Dow Chemical Company) having a particle size of 0.721 μm, and the obtained suspension was centrifuged at 4,000 r.p.m. for 20 minutes. The thus separated precipitate was suspended in 250 ml of said buffer solution and then centrifuged under the same conditions mentioned above, and the precipitate was collected. Then 250 ml of said buffer solution containing 88 mg of the previously obtained conjugate was added to the eventually collected precipitation (latex particles), the obtained suspension was kept at 37° C. for two hours, and then the suspension was centrifuged to collect the precipitate. The precipitate was resuspended in 250 ml of said buffer solution and centrifuged under the same conditions mentioned above and these processes were repeated once again. The thus obtained precipitate was resuspended in 250 ml of said buffer solution, and then sodium azide was added thereto so that the eventual concentration thereof came to be about 0.1%. Thus 250 ml of about 2% concentration HC-21-HS-HSA sensitized latex particle suspension was obtained.

Then 0.05 ml of 0.1 nmole hydrocortisone was mixed with 0.05 ml of diluted antibody which was prepared in like manner as that in the Test 1 and diluted with said buffer solution to give a titer of 0.1 nmole HC-21-HS equivalent/ml on a glass slide, and then 0.1 ml of the previously obtained sensitized latex particle suspension was mixed therewith. No agglutination was observed even after ten minutes. However when 0.05 ml of 0.05 nmole/ml hydrocortisone and 0.05 ml of said diluted anti-body was mixed and then 0.1 ml of said sensitized latex particle suspension was added on a glass slide, agglutination was observed within 2-3 minutes. The titer of the latex reagent of this example was determined to be nmole 0.05 HC-21-HS equivalent/ml.

We claim:

1. A method for preparation of a latex reagent containing latex particles sensitized with a steroid-serum albumin conjugate and suitable for immunochumical detection of steroid contained in human body fluid or excreted fluid, which comprises
    preparing steroid-serum albumin conjugate by reacting a steroid with a serum albumin in a ratio between 0.5 mole/mole serum albumin–7.0 mole/mole serum albumin, and
    preparing sensitized latex particles by sensitizing immunologically inert latex particles with said steroid-serum albumin conjugate.

2. The method of claim 1 wherein the sensitization of the latex particles with the conjugate is performed using a quantity of said conjugate which does not cause non-specific agglutination due to the sensitized latex particles themselves.

3. The method of claim 1, wherein
said serum albumin is selected from the group consisting of bovine serum albumin, equine serum albumin, sheep serum albumin, rabbit serum albumin and human serum albumin.

4. The method of claim 1, wherein
said latex particles are selected from the group consisting of polystyrene, polybutadiene and styrene-butadiene copolymer latex particles.

5. The method of claim 1 wherein
said steroid used to prepare the conjugate can provoke an antigen-antibody reaction with the antibody for which a compound selected from the group consisting of estrogen and its metabolites, progesterone and its metabolites, androgen and its metabolites, and 17-hydroxycorticosterone and its metabolites can act as a hapten.

6. The method of claim 5, wherein
said steroid used for preparation of the conjugate is selected from the group consisting of estrogen, progesterone, androgen, 17-hydroxycorticosterone and their metabolites.

7. The method of claim 1, wherein
the particle size of said latex particles is within the range 0.234 μm–0.721 μm, and the quantity of said conjugate utilized for sensitization of said latex particles is within the range 0.3 μmole/1 g latex particles–1.1 μmole/1 g latex particles.

8. A latex reagent comprising latex particles sensitized with steroid-serum albumin conjugate and suitable for immunochemical detection of steroid contained in human body fluid or excreted fluid, wherein said conjugate has a steroid bonding number in the range 0.5–7.0 molecules per molecule of serum albumin, and said latex particles are sensitized with an effective amount of said conjugate to avoid non-specific agglutination but to cause agglutination due to antigen-antibody reaction between said latex reagent and the antibody for which the steroid to be detected may act as a hapten.

9. The latex reagent of claim 8, wherein
the serum albumin moiety of said steroid-serum albumin conjugate is selected from the group consisting of bovine serum albumin, equine serum albumin, sheep serum albumin, rabbit serum albumin, and human serum albumin.

10. The latex reagent of claim 8, wherein
said latex particles are selected from the group consisting of polystyrene, polybutadiene and styrene-butadiene copolymer latex particles.

11. The latex reagent of claim 8, wherein
the steroid moiety of said steroid-serum albumin conjugate is a steroid capable of provoking an antigen-antibody reaction with the antibody for which a compound selected from the group consisting of estrogen and its metabolites, progesterone and its metabolites, androgen and its metabolites, and 17-hydroxycorticosterone and its metabolites can act as a hapten.

12. The latex reagent of claim 11, wherein
said steroid is selected from the group consisting of estrogen, progesterone, androgen, 17-hydroxycorticosterone and their metabolites.

13. The latex reagent of claim 8, wherein
the particle size of said latex is within the range 0.234 μm–0.721 μm, and the quantity of said conjugate utilized for sensitization of said latex particles is within the range 0.3 μmole/1 g latex particles–1.1 μmole/1 g latex particles.

14. In a method for the immunochemical detection of a steroid compound and/or metabolites thereof present in human body fluid or excreted fluid by forming a conjugate of a steroid and a protein material, forming sensitized latex particles by absorbing said conjugate on latex particles, obtaining an antiserum or antibody by injecting an animal with said conjugate and thereafter separating said antiserum or antibody from the blood of said animal and determining the presence of said steroid compound in a sample of body fluid by an agglutination reaction in the presence of said antiserum or antibody and said sensitized latex particles, the improvement comprising:

increasing the sensitivity of said method by employing a conjugate having a steroid to serum albumin mole ratio ranging from 0.5 to 7.0.

15. The method of claim 14, wherein said serum albumin is selected from the group consisting of bovine serum albumin, equine serum albumin, sheep serum albumin, rabbit serum albumin and human serum albumin.

16. The method of claim 14, wherein said steroid used for preparation of the conjugate is selected from the group consisting of estrogen, progesterone, androgen, 17-hydroxycorticosterone and their metabolites.

* * * * *